United States Patent [19]

Suzuki et al.

[11] 4,426,337

[45] Jan. 17, 1984

[54] METHOD FOR PRODUCING SEAMLESS MATERIAL-FILLED CAPSULE AND MINIATURE CAPSULES

[75] Inventors: Toshiyuki Suzuki, Amagasaki; Funiaki Matsumura, Ya'o; Hiroshi Maeda, Sakai; Akira Imai, Higashi-Osaka; Nobuo Kurokawa, Nara, all of Japan

[73] Assignee: Morishita Jintan Company, Limited, Osaka, Japan

[21] Appl. No.: 403,715

[22] Filed: Jul. 30, 1982

Related U.S. Application Data

[60] Continuation of Ser. No. 170,964, Jul. 18, 1980, abandoned, which is a division of Ser. No. 962,043, Nov. 20, 1978, Pat. No. 4,251,195, which is a continuation of Ser. No. 749,755, Dec. 13, 1976, abandoned.

[30] Foreign Application Priority Data

Dec. 26, 1975 [JP] Japan ............................... 50-157935
Jun. 4, 1976 [JP] Japan ............................... 51-65308
Jun. 4, 1976 [JP] Japan ............................... 51-65309

[51] Int. Cl.³ .......................... B29F 3/10; B29C 23/00
[52] U.S. Cl. ........................................... 264/4; 264/7; 264/9; 425/6
[58] Field of Search ....................... 264/4, 7, 9; 425/5, 425/6, 70, 133.1, 804, DIG. 101

[56] References Cited

U.S. PATENT DOCUMENTS

| | | | |
|---|---|---|---|
| 2,379,816 | 7/1945 | Mafba | 264/4 |
| 2,911,672 | 11/1959 | Dorens et al. | 264/4 |
| 3,123,855 | 3/1964 | Fischer et al. | 425/6 |
| 3,397,258 | 8/1968 | Williams | 264/9 |
| 3,962,383 | 6/1976 | Hagwara et al. | 425/5 |

Primary Examiner—James B. Lowe
Attorney, Agent, or Firm—Robert E. Burns; Emmanuel J. Lobato; Bruce L. Adams

[57] ABSTRACT

A vibrating body is so provided as to surround a jet stream composed of a capsule film material and a capsule filler material extruded from the orifice of two coaxial conduits positioned in a cooling liquid medium. The vibrating body can be controlled in reciprocating vibration in the upward and downward directions whereby it is possible to produce waves in the cooling liquid medium which are most suitable for obtaining the required diameter of capsules and the required speed of manufacture. The jet stream is formed into spherical capsule drops at markedly increased speed of manufacture owing to the control of vibration of the vibrating body and interfacial tension.

The method for obtaining seamless capsules can ensure the possibility of manufacture of very small capsules, i.e. miniature capsules by mass production which has never been accomplished satisfactorily by the conventional methods and apparatus in the industry. Thus, it is made possible by this method to manufacture not only common seamless capsules but also very small seamless capsules, for example, such as oral refrigerants and spice condiments.

8 Claims, 3 Drawing Figures

METHOD FOR PRODUCING SEAMLESS MATERIAL-FILLED CAPSULE AND MINIATURE CAPSULES

This is a continuation application of now-abandoned Ser. No. 170,964 filed July 18, 1980, which is a division of Ser. No. 962,043, now U.S. Pat. No. 4,251,195 and which was filed Nov. 20, 1978 as a continuation application of Ser. No. 749,755 filed Dec. 13, 1976, now abandoned.

BACKGROUND OF THE INVENTION

1. Field of the Invention

This invention relates to a method for manufacturing seamless material-filled capsules, and miniature capsules having the values of particle diameter 0.5-4 mm, weight 1-30 mg, film percentage 5-30% and film thickness 0.05-0.2 mm.

2. Description of the Prior Art

According to a conventional apparatus for manufacturing seamless material-filled capsules, namely, in producing capsules of about 100 mg-500 mg by weight per capsule at a speed of manufacture, 4-10 capsules per second, the speed of manufacture has been found common to obtain 30 capsules per orifice per second as a maximum in the case of manufacturing small capsules of about 10 mg by weight per capsule.

Therefore, in manufacturing about 30 capsules per second by a conventional manufacturing apparatus, there occurs the problem of a capsule film material, capsule filler material as well as the influence of interfacial tension and restriction of manufacture due to much disturbance that the number of capsules per orifice has to be restricted and eventually both operation and apparatus are most apt to become complicated in many respects until the system of mass production of capsules is likely to be decreased in function. In fact, such tendency has become very large as particularly small capsules are to be manufactured.

In view of a conventional apparatus for manufacturing material-filled capsules and in order to improve the speed of manufacture in such a case, the applicant of the present application has carried out various tests and researches. As a result, the applicant has succeeded in developing a method which is capable of manufacturing seamless material-filled capsules in the order of one figure larger than the maximal number of capsules to be manufactured per second by a conventional apparatus and at the same time, effecting the mass production of seamless material-filled capsules always of uniform capsule diameter and film thickness in a very rapid manner, regardless of the size of capsules.

Moreover, the seamless material-filled capsules thus obtained by the method of the present invention can occur as miniature capsules, namely, in the form of much smaller capsules than capsules obtained by a conventional apparatus.

By employing the method of the present invention, it is possible to improve the rate of manufacture of seamless material-filled capsules whereby mass production of capsules can be promoted to such an extent as has never been accomplished by known methods. Indeed, as explained hereinbefore, it has become possible to attain the mass production of miniature capsules very easily, which as heretofore has been considered difficult by a conventional apparatus, namely, miniature capsules of capsule diameter 0.5-4 mm, weight 1-30 mg, film percentage 5-30 % and film thickness 0.05-0.2 mm.

Hitherto, capsules after formed as much have no been utilised satisfactorily to comply with their original object for use, because of various problems and unfavorable conditions such as the size of capsules and film thickness.

Now, material-filled capsules in the form of miniature capsules made according to the present invention can be used extensively in cases where, otherwise, the above mentioned bad results would usually prevail. Namely, by making material-filled capsules into miniature capsules, the extent of their utilisation has become very wide and high in scope.

SUMMARY OF THE INVENTION

A first object of the present invention consists in providing a method for manufacturing seamless double capsules consisting of a liquid capsule film material and a capsule filler material using the open ended two concentric conduits as on orifice. The film material is set core in a cooling liquid medium, wherein a ring body or vibrating body in the form of a cylinder is provided, just below, and a distance apart from, the lower end of the open ends of two coaxial conduits in the cooling liquid medium as to surround a jet stream of the capsule film material extruded from the orifice into the cooling liquid medium and to vibrate up and down with certain frequency along the lengthwise direction of the jet stream.

The second object of the present invention consists in providing a method capable of manufacturing seamless material-filled capsules at the rate of one figure larger than the maximal number of capsules per second, which has been obtained by any method of the prior art.

The third object of the present invention consists in considerably improving the mass production of capsules of prior art by largely increasing the speed of manufacture of seamless material-filled capsules.

The fourth object of the present invention consists in providing seamless material-filled capsules always of uniform capsule diameter and uniform film thickness, regardless of the size of the capsules.

The fifth object of the present invention consists in ensuring the mass production of miniature capsules having such values as capsule diameter 0.5-4 mm, weight 1-30 mg, film percentage 5-30 % and film thickness 0.05-0.2 mm, which are much less than those of conventional capsules.

The sixth object of the present invention consists in obtaining the mass production of breath freshener and spice condiments in the form of miniature capsules as mentioned above.

BRIEF DESCRIPTION OF THE DRAWING

FIG. 2 is a view to show a vibrating body in the form of a ring. FIG. 3 is a view to show a vibrating body in the form of a cylinder.

DESCRIPTION OF THE PREFERRED EMBODIMENTS

Figure 1:
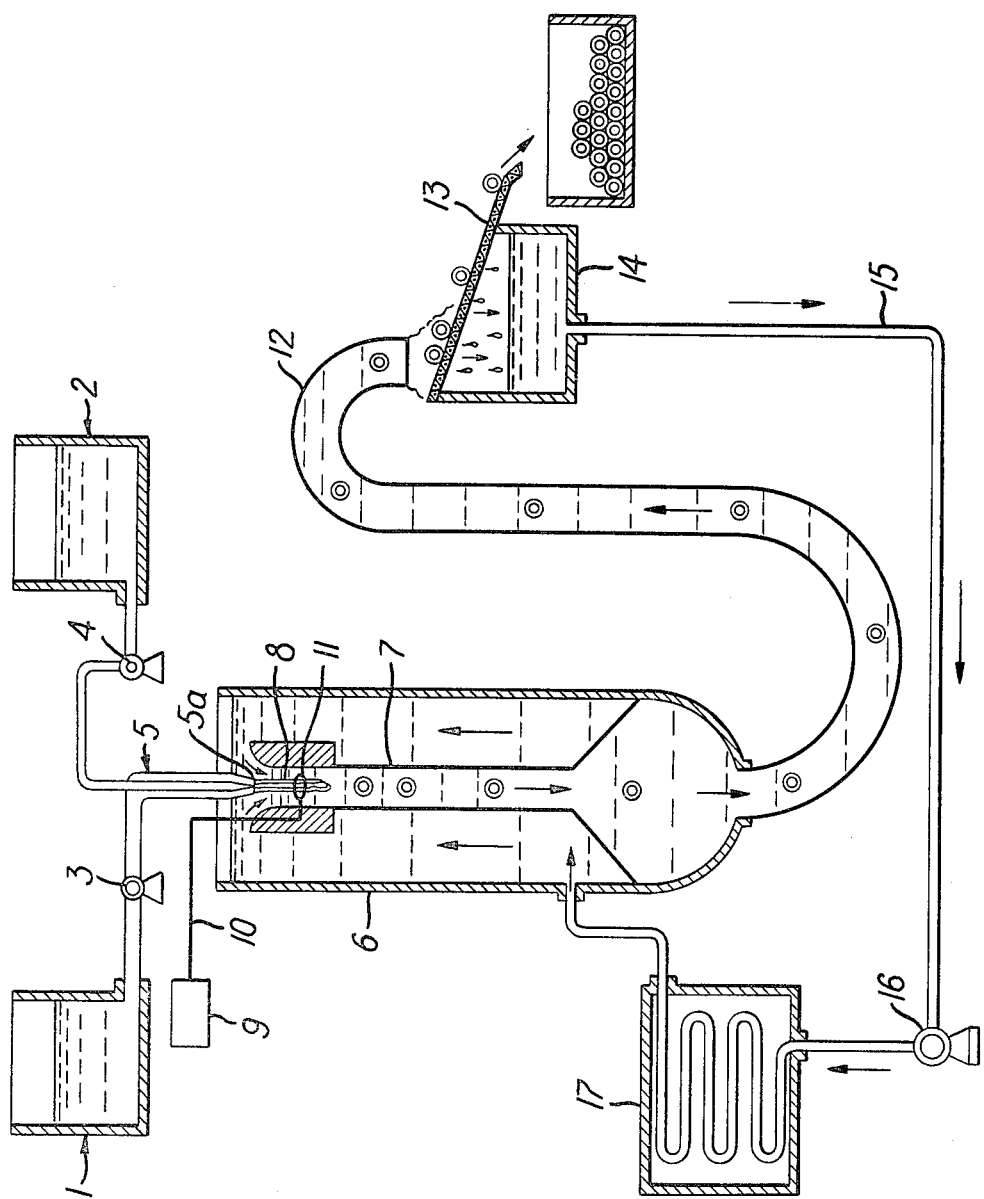
FIG. 1 is a general side elevation view on apparatus for manufacturing seamless material-filled capsules, according to the present invention, which apparatus is capable of largely increasing the speed of manufacture of seamless material-filled capsules and obtaining seamless material-filled capsules in the form of miniature capsules.

The aforesaid objects and characteristics of the present invention will be understood accurately by way of the preferred embodiments with reference to the apparatus as shown in the accompanying drawings and their explanation in detail.

Firstly, the apparatus and method of the present invention will be explained with reference to FIG. 1.

Gelatin, D-sorbit, gum Arabic and water as a film material of capsule are stored in a tank 1. This tank 1 is connected to the outer cylindrical portion of a double cylindrical pipe 5 through a pump 3. Vegetable oil used as a capsule filler material is stored in a tank 2. This tank 2 is connected to the inner pipe of the coaxial conduits 5 through a pump 4. The lower end 5a of the conduits forms a capsule-forming orifice opening downwardly in a capsule-forming cylinder 7 disposed in a main body 6 of a cooler and the capsule-forming cylinder has a uniform internal diameter at every point. Beneath the lower end or orifice 5a and a distance apart therefrom is provided a ring 11 or a cylinder 11a integral with a vibration-transmit lever 10 with a vibrator 9 so as to surround a jet stream 8 extruded from the double cylindrical orifice 5a into a cooling liquid medium in the lengthwise direction of jet stream 8. In connection with the extruded amount of the jet stream 8 is provided a recovery pipe 12 to promote the formation of capsules while cooling material-filled capsules continuously and beneath the discharge outlet of the capsule recovery pipe 12 is provided a net-like separator 13 for separating the finished capsules from the cooling liquid medium. Also beneath the separator 13 is provided a reservoir 14 of cooling liquid medium and the reservoir 14 is provided with a circulation pipe 15 for recovering the cooling liquid medium. The circulation pipe 15 is arranged in such a manner that the cooling liquid medium can be recycled to the main body 6 through a circulation pump 16 and a heat exchanger 17 for maintaining the temperature of the cooling liquid medium at a constant level.

With respect to the manufacture of seamless material-filled capsules at a quickened rate using the present method, the present invention will be explained hereinafter.

A solution of capsule-film material composed of gelatin, D-sorbit, gum Arbic and water enters the outer cylindrical portion of the double coaxial conduits 5 of from the tank 1 through the pump 3. A capsule filler material composed of vegetable oil enters the inter cylindrical portion or conduit of the double pipe 5 from the tank 2 through the pump 4.

The aforesaid two solutions are extruded from the lower end 5a double cylndrical orifice and are formed into the jet streams 8 at the orifice and flowed in a stream of cooling liquid medium and detailed to descend in the capsule-forming cylinder 7. In this case, the flow speed of the cooling liquid medium in the capsule-forming cylinder 7 is adjusted to the most suitable speed which can be calculated from the diameter and number of capsules to be manufactured.

While the jet stream 8 remains as one of a uniform diameter, waves are caused or developed in the cooling liquid medium by means of the ring 11 vibrating up and down with a definite frequency due to the vibration of the vibrator 9. Upon receiving the influence of the waves of cooling liquid medium thus caused, the jet stream 8 too is sure made to develop waves.

While descending further, the jet stream 8 is squeezed and cut off drop by drop so as to become spherical capsule drops of uniform diameter due to interfacial tension.

Subsequently, the capsule drops thus formed keep descending in the capsule recovery pipe 12 and are cooled sufficiently and after the solution of capsule-film material has been solidified, the capsules and the cooling liquid medium are separated from each other by means of the separator so that the former can be obtained as seamless material-filled capsules here.

The cooling liquid medium thus separated through the separator 13 flows through a circulation pipe 15, and is fed into the heat exchanger through the pump 16, and after being cooled there, it will enter the capsule-forming cylinder 7 again for purposes of circulation. Owing to such circulation, it is possible to obtain seamless material-filled capsules of uniform diameter by mass production at a markedly increased speed.

Figure 2:
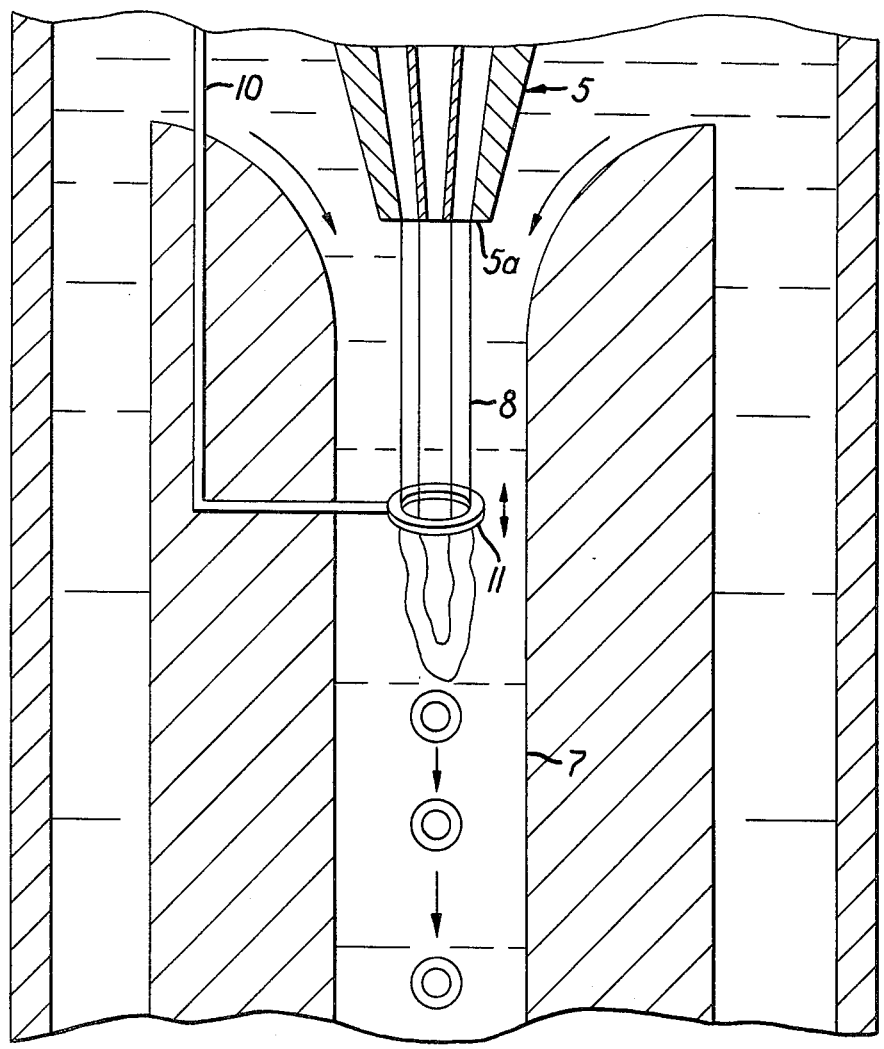
FIGS. 2 and 3 are cross-sectional views on an enlarged scale of parts of the present invention. Namely.

FIG. 2 is a view showing an enlarged view of environs of the orifice and vibrating ring of FIG. 1.

Figure 3:
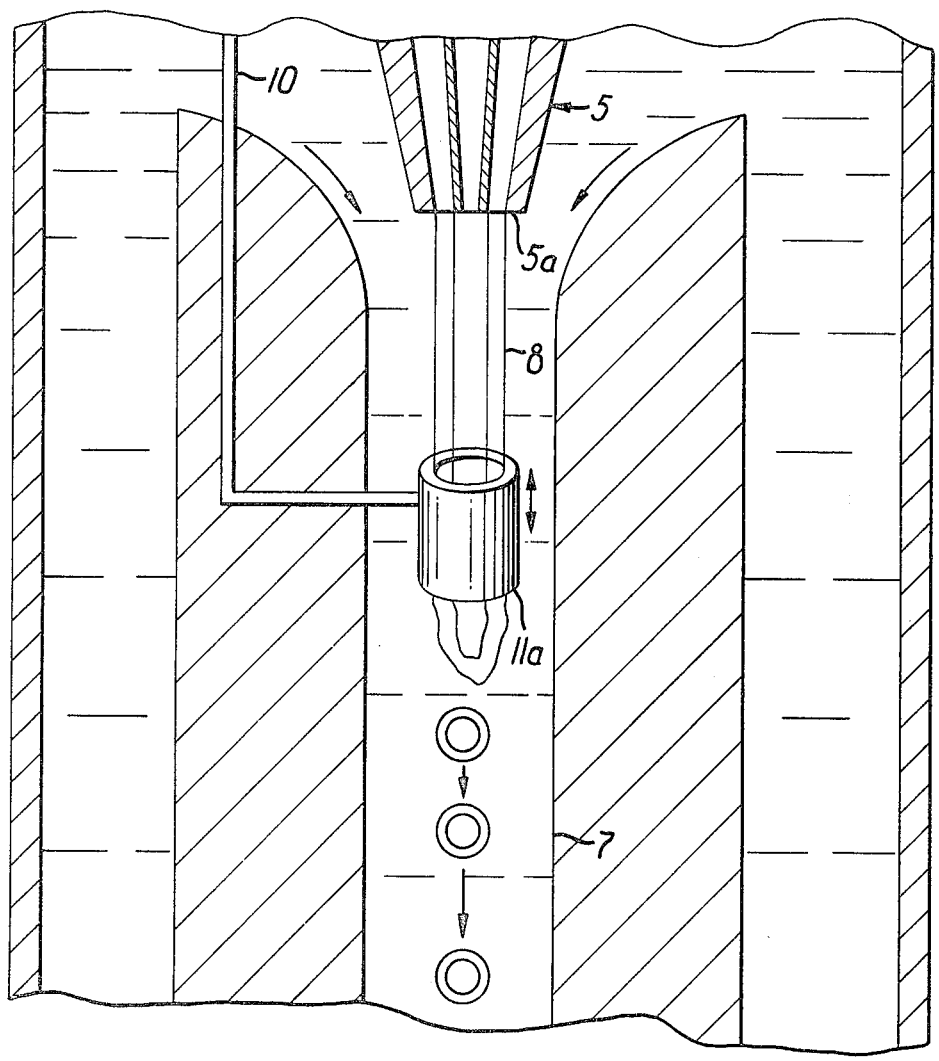

FIG. 3 is a view showing also an enlarged view of environs of the orifice and a thinwall vibrating cylinder in place of a vibrating ring.

An explanation will be extended to miniature capsules which can be obtained by the apparatus of the present invention for manufacturing seamless material-filled capsules with the possibility of largely increasing the speed of manufacture. Namely, by so-called miniature capsules here are meant capsules of such values as those having a capsule diameter 0.5–5 mm, weight 1–30 mg, film percentage 5–30 % and film thickness of 0.05–0.2 mm.

The usual size of the capsules of prior art are of globular diameter, more than 4 mm, weight, more than 50 mg, film percentage, more than 30 % and film thickness, more than 0.2 mm.

In comparing the values of both kinds of capsules, it is found that the difference between them is very considerable. Thus, the present invention has led to the possibility of mass production of miniature capsules in an easy and rapid manner, which fact should be called epochmaking in the industry of capsules for practical use.

Owing to the fact that it is possible to obtain miniature capsules by the method of the present invention, an extremely high rate of utilization of such miniature capsules has been ensured, whereas capsules of such large size and film thickness of the prior art, even after being formed into so-called capsules, may not correctly be called capsules. Now then, spice condiments in the form of miniature capsules will be explained.

For example, in the case of spice condiments for use as a sprinkle additive to instant food, the globular diameter of conventional capsules is so large, their form is so unfavourable and they are so heavy that the effect of spice in such capsules will be lost as unsuitable for use. On the other hand, the film of conventional capsules is so thick and slow in being dissolved that the effect of spice in them will be developed only very late thus leading to unfavorable results and almost losing the original value of their utilization in most cases.

When using a single condiment in the form of a capsule of the usual size, each globule becomes large. When attempting to enhance the concentration of such condiment, its taste will become too strong. Also in point of uniformity of taste, only one to three capsules for addition will be maximal so that they cannot be used satisfactorily after all because of the failure of uniformity of taste.

In contrast, in the case of preparing spice condiments in miniature capsules that can be obtained by the apparatus of the present invention for manufacturing material-filled capsules with the possibility of increasing the speed of manufacture, it is possible to obtain very large advantages, in points of carrying, preservation, cleanliness, handling, estimate of amount and accuracy for use. Moreover, the film of the miniature capsules is so thin that they can be dissolved very rapidly.

Here, two preferred embodiments of spice condiments in miniature capsules will be exemplified as follows.

Preferred embodiment 1:

For use as space for addition to instant noodle or cup noodle. Spice oil and sesame oil are mixed in the ratio of 7:3 to produce 14 mg of the resulting mixture by weight, which is enclosed in a film of 6 mg by weight of gelatin, D-sorbit and refined water to produce a miniature capsule.

Preferred embodiment 2:

For use as liquid-like spice for addition to the aforesaid instant foods. Chinese oil, garlic oil and ginger oil are mixed in the ratios of 4:3:3 to obtain 14 mg of the resulting mixture by weight which is enclosed in a film of 6 mg by weight of gelatin, D-sorbit and refined water to produce a miniature capsule.

The method of manufacturing miniature capsules by the apparatus shown in FIG. 1 using the materials shown in the aforesaid preferred embodiments will be explained hereinbelow.

In FIG. 1, a solution composed of 15 % gelatin, 5 % glycerine and 80 % water was stored in the tank 1, heated to 70° C. and fed to the coaxial conduits 5 of at the rate of 2 g per second by means of the pump. A solution of mixture of spice oil and sesame oil in the ratio of 7:3 was stored in the tank 2 and fed to the orifice 5a at the rate of 1.4 g per second by means of the pump 4. The vibrator 9 was vibrated at a frequency of 200 Hz and adjusted so that the ring 11 could be vibrated at the whole amplitude 0.5 mm. The ring 11 was disposed in a position about 30 mm below the lower end of the orifice 5a. The internal diameter of the capsule-firming cylinder 7 was 22 mm and a cooling liquid medium was adapted to cool vegetable oil to 0° C. and to flow at the rate of 80 cm on an average per second.

In this manner, it was possible to produce 200 seamless material-filled miniature capsules per second, each capsule of 10 mg by total weight containing 7 mg of spice oil and sesame oil.

Now, oral refrigerants or breath refreshers in the form of miniature capsules of the present invention will be explained hereinafter.

Since conventional capsules of oral refrigerants have too large a size and too thick a film, they are slow in being dissolved in the mouth and accordingly, their effect is developed slowly.

Even after being dissolved, the capsule feels foreign to the mouth and moreover, because of the capsule weighing as much as 100 mg, it is necessary to dilute peppermint oil with other oil so that the inherent refreshing feel of peppermint may be lost and the development of taste may cease until even an oil odor has occurred.

In contrast, when preparing a breath refresher in miniature capsules obtained by the method of the present invention, the above-mentioned disadvantages can be completely eliminated. Namely, in such a case, by dint of the thin film of each miniature capsule, the capsule will be dissolved rapidly in the mouth and never feels foreign to the mouth. At the same time, since peppermint oil only as an oral refresher can be enclosed in a miniature capsule of 10 mg by weight, the fragrance and taste of its contents are found very good and such miniature capsules are easy to carry and handle with good preservative properties. Two preferred embodiments of breath refresher in miniature capsules will be explained hereinbelow.

Preferred embodiment 1:

Peppermint oil was enclosed in a film composed of D-sorbit and refined water to result in a capsule of 10 mg by weight consisting of 8 mg as contents of peppermint oil and 2 mg of film.

Preferred embodiment 2:

A miniature capsule was introduced as a single-nuclear double capsule. It was 30 mg heavy enclosing a mixture of orange oil, granule sugar and edible oil in the ratios of 35:30:35, the contents weighting 21 mg and being enclosed in an intermediate layer of 4.5 mg by weight in the form of a mixture of gelatin, refined vegetable oil, D-sorbit and refined water in the ratios of 10:30:2:58 and then the intermediate layer was enclosed in an outer layer of 4.5 mg by weight in the form of a mixture of gelatin, D-sorbit and refined water in the ratios of 20:10:70 so that the resulting capsule occurred in the form of the above mentioned single-nuclear double capsule.

A single-layer miniature capsule in cases a breath refresher can be obtained by the same method and apparatus as those of spice condiments. Lastly, all effects obtained by the method and apparatus of the present invention will be explained hereinafter.

(1) By virtue of the method of the present invention, it is possible to quicken the speed of manufacture of seamless material-filled capsules to a large extent and to ensure the mass production of seamless material-filled capsules as high as one figure larger than the maximal number of capsules per second which have been heretofore obtained by conventional methods and apparatus. Thus, this excellent effect has led to improving the system of mass production of capsules which has never been attained by conventional apparatus.

(2) Regardless of the size of capsules, it is possible to always obtain seamless material-filled capsules of uniform diameter and film thickness.

(3) It is possible to obtain such an effect as the mass production of miniature capsules of diameter 0.5–4 mm, weight 1–30 mg, film percentage 5–30 % and film thickness 0.05–0.2 mm. This outstanding effect has led to the extensive use of miniature capsules in cases where capsules of conventinal film thickness fail to develop a market and to an answer to their original requirements for use. Thus, miniature capsules of the present invention for use in the fields of condiments, breath refreshers, medicines, foods, luxuries and bath agents will be highly appreciated and their practical value will prove very significant.

What is claimed is:

1. A method for making miniature capsules comprising extruding filler-contents for capsules and delivering the filler-contents as an extruded stream, extruding a film sleeve of a liquid settable coating material circumferentially of said extruded stream of filler-contents and in the same flow direction for coating and enclosing droplets of said filler-contents, flowing a flow of cooling liquid along a path of travel parallel to and circumferentially of said extruded stream of filler-contents and the film sleeve of the liquid settable coating material, reciprocating an annular member in the cooling liquid circumferentially of the film sleeve of liquid settable coating material and the extruded stream of filler-contents while in the path of travel wherein the cooling fluid, the extruded film sleeve and the extruded stream of filler-contents are flowing in parallel and reciprocating the annular member in opposite directions axially of said path of travel to develop waves in said cooling liquid effective to develop discrete droplets of said filler-contents enclosed within the settable coating material, and setting the coating material enclosing the droplets of said filler-contents to form miniature capsules.

2. A method of making miniature capsules according to claim 1, in which said flow direction is a downward direction.

3. A method of making miniature capsules according to claim 1, in which reciprocation of said annular member is at different frequencies.

4. A method for making miniature capsules comprising, extruding filler-contents for capsules and delivering the filler-contents as an extruded stream, extruding a film sleeve of a liquid settable coating material circumferentially of said extruding stream of filler-contents and in the same flow direction for coating and enclosing droplets of said filler-contents, flowing a flow of cooling liquid along a circumferentially enclosed path of axial travel parallel to and circumferentially of said extruded stream of filler-contents and the film sleeve of the liquid settable coating material, reciprocating an annular member in the cooling liquid circumferentially of the film sleeve of the liquid settable coating material and the extruded stream of filler-contents while in the enclosed path of travel wherein the cooling fluid, the extended film sleeve and the extended stream of filler-contents are flowing in parallel and reciprocating the annular member in opposite directions axially of said path of travel to develop waves in said cooling liquid effective to develop discrete droplets of said filler-contents enclosed within the settable coating material, and setting the coating material to form miniature capsules.

5. A method of making miniature capsules according to claim 4, in which said waves in said cooling liquid in said enclosed path travel radially inwardly of said tubular member and axially thereof squeezing the film sleeve and the droplets are formed due to interfacial tension.

6. A method of making miniature capsules comprising, extruding filler-contents for capsules and deliverying the filler-contents as an extruded stream, while extruding said extruded stream simultaneously extruding a film sleeve of a liquid settable coating material circumferentially of said extended stream of filler-contents and in the same flow direction for coating and enclosing droplets of said filler-contents, flowing a flow of cooling liquid along a circumferentially enclosed path of axial travel parallel to and circumferentially of said extruded stream of filler-contents and the film sleeve of the liquid settable coating material, reciprocating an annular member in the cooling liquid circumferentially of the film sleeve of the liquid settable coating material and the extruded stream of filler-contents while in the enclosed path of travel wherein the cooling fluid, the extruded film sleeve and the extended stream of filler-contents are flowing in parallel and reciprocating the annular member in opposite directions axially of said path of travel to develop waves in said cooling liquid to develop discrete droplets of said filler-contents enclosed within the settable coating material, and setting the coating material to form miniature capsules.

7. A method of making miniature capsules according to claim 6, in which said setting takes place in the cooling liquid.

8. A method of making miniature capsules according to claim 7, including recoverying the miniature capsules from the cooling liquid.

* * * * *